US010206797B2

(12) United States Patent
Steadham et al.

(10) Patent No.: US 10,206,797 B2
(45) Date of Patent: *Feb. 19, 2019

(54) HELICAL HIGH FATIGUE STENT-GRAFT

(71) Applicant: C.R. Bard, Inc., Tempe, AZ (US)

(72) Inventors: Chris Steadham, Harrisburg, NC (US); David L. Bogert, Labelle, FL (US)

(73) Assignee: C. R. Bard, Inc., Murray Hill, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/415,848

(22) Filed: Jan. 25, 2017

(65) Prior Publication Data
US 2017/0128241 A1 May 11, 2017

Related U.S. Application Data

(60) Continuation of application No. 14/839,802, filed on Aug. 28, 2015, now Pat. No. 9,585,775, which is a
(Continued)

(51) Int. Cl.
*A61F 2/06* (2013.01)
*A61F 2/88* (2006.01)
(Continued)

(52) U.S. Cl.
CPC .................. *A61F 2/88* (2013.01); *A61F 2/07* (2013.01); *A61F 2/82* (2013.01); *A61F 2/89* (2013.01); *A61F 2/915* (2013.01); *A61F 2002/072* (2013.01); *A61F 2002/075* (2013.01); *A61F 2210/0076* (2013.01); *A61F 2220/005* (2013.01); *A61F 2220/0075* (2013.01); *A61F 2230/0069* (2013.01); *A61F 2250/0096* (2013.01)

(58) Field of Classification Search
CPC .... A61F 2/07; A61F 2/88; A61F 2/885; A61F 2/89; A61F 2/915; A61F 2002/072; A61F 2002/075
See application file for complete search history.

(56) References Cited

U.S. PATENT DOCUMENTS 6,013,854 A * 1/2000 Moriuchi ................. A61F 2/91
606/194
6,346,119 B1 2/2002 Kuwahara et al.
(Continued)

FOREIGN PATENT DOCUMENTS

WO 199838946 A1 9/1998

OTHER PUBLICATIONS

PCT/US2007/017985 filed Aug. 14, 2007 International Preliminary Report on Patentability and Written Opinion date. Feb. 26, 2008.
(Continued)

*Primary Examiner* — Brian Dukert
(74) *Attorney, Agent, or Firm* — Rutan & Tucker, LLP

(57) ABSTRACT

An implantable prosthesis, including a generally tubular substrate and a continuous shape memory member disposed over the outer surface of the substrate. The shape memory member may include a series of zig-zag struts alternating between a first strut with a first length and a second strut with a second length different from the first length. A graft member may be positioned over the substrate and shape memory member.

20 Claims, 2 Drawing Sheets

Related U.S. Application Data division of application No. 14/185,653, filed on Feb. 20, 2014, now abandoned, which is a division of application No. 12/439,156, filed as application No. PCT/US2007/017985 on Aug. 14, 2007, now Pat. No. 8,696,733.

(60) Provisional application No. 60/840,868, filed on Aug. 29, 2006.

(51) Int. Cl.
*A61F 2/07* (2013.01)
*A61F 2/915* (2013.01)
*A61F 2/89* (2013.01)
*A61F 2/82* (2013.01)

(56) References Cited

U.S. PATENT DOCUMENTS

| | | |
|---|---|---|
| 6,352,552 B1 | 3/2002 | Levinson et al. |
| 6,524,334 B1 | 2/2003 | Thompson |
| 6,626,939 B1 | 9/2003 | Burnside et al. |
| 6,770,087 B2 * | 8/2004 | Layne ............... A61F 2/07 623/1.13 |
| 6,911,040 B2 | 6/2005 | Johnson et al. |
| 8,696,733 B2 | 4/2014 | Bogert et al. |
| 2002/0065550 A1 | 5/2002 | Smith |
| 2003/0139806 A1 * | 7/2003 | Haverkost ............. A61F 2/06 623/1.33 |
| 2006/0064159 A1 | 3/2006 | Porter et al. |
| 2014/0172073 A1 | 6/2014 | Steadham et al. |

OTHER PUBLICATIONS

PCT/US2007/017985 filed Aug. 14, 2007 International Search Report dated Feb. 26, 2008.
U.S. Appl. No. 12/439,156, filed Jul. 15, 2009 Final Office Action dated Feb. 3, 2012.
U.S. Appl. No. 12/439,156, filed Jul. 15, 2009 Non-Final Office Action dated Aug. 22, 2011.
U.S. Appl. No. 12/439,156, filed Jul. 15, 2009 Non-Final Office Action dated Feb. 17, 2011.
U.S. Appl. No. 12/439,156, filed Jul. 15, 2009 Non-Final Office Action dated Jun. 13, 2013.
U.S. Appl. No. 12/439,156, filed Jul. 15, 2009 Notice of Allowance dated Nov. 29, 2013.

* cited by examiner

HELICAL HIGH FATIGUE STENT-GRAFT

PRIORITY

This application is a continuation of U.S. patent application Ser. No. 14/839,802, filed Aug. 8, 2015, now U.S. Pat. No. 9,585,775, which is a division of U.S. patent application Ser. No. 14/185,653, filed Feb. 20, 2014, which is a division of U.S. patent application Ser. No. 12/439,156, now U.S. Pat. No. 8,696,733, filed as a U.S. national stage application under 35 USC § 371 of International Application No. PCT/US2007/017985, filed Aug. 14, 2007, which claims the benefit of priority to U.S. Provisional Application No. 60/840,868, filed Aug. 29, 2006, each of which is incorporated by reference into this application as if fully set forth herein.

BACKGROUND

Intraluminal prostheses used to maintain, open, or dilate blood vessels are commonly known as stents. Stent constructions generally include lattice type cylindrical frames that define a plurality of openings. Common frameworks for stents include, for example, individual rings linked along the length of the stent by a linking member, a continuous helically wrapped member (that may include one or more linking members), a braid or a mesh formed into a tubular structure, and a series of interconnected struts. Stents may be formed by arranging one or more members in a pattern along a longitudinal axis to define essentially a cylinder and connecting the one or more members or otherwise affixing them in position (e.g., interconnecting with a filament). Stents may also be formed by cutting openings into a tube of material (e.g., shape memory).

Stents may have self-expanding and/or balloon expandable properties. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube. Grafts can also be created from fibers woven or knitted into a generally tubular shape.

It is known in the art to use stents in combination with vascular grafts to form stent-grafts. Because stent-grafts are often intraluminally deployed in vessels of varying sizes and tortuosity, flexibility can be an important consideration. Flexibility can be imparted to a stent-graft in a variety of ways, including, for example, connection of the stent to the one or more graft layers, configuration of the stent and/or graft layer(s), spacing of the stent struts, rings, or members along the length of the graft(s), etc. For example, U.S. Pat. No. 6,398,803 and U.S. Pat. No. 6,770,087 to Layne et al., which are incorporated by reference in their entirety into this application, describe a graft layer with openings to enhance flexibility. Another important consideration in the design of a stent-graft is the ability of the stent to withstand stress and fatigue, caused, for example, by plastic deformations occurring at strut junctions when the stent is subjected to circumferential forces. Stent strength can be enhanced through material choice, stent configuration, arrangement and configuration of graft layers, etc.

The following references relate to stents and stent-grafts: U.S. Pat. No. 5,282,824 to Gianturco; U.S. Pat. No. 5,507,767 to Maeda et al.; U.S. Pat. No. 5,545,211 to An et al.; U.S. Pat. No. 5,591,195 to Taheri et al.; U.S. Pat. No. 6,673,103 to Golds et al.; and U.S. Pat. No. 6,984,243 to Dwyer et al., each of which is incorporated by reference in its entirety into this application.

Applicants have recognized that it would be desirable to provide a stent-graft that is both flexible and able to maintain strength under high stress/fatigue environments, embodiments of which are described herein along with methods of making same.

BRIEF SUMMARY

Accordingly, in one embodiment, an implantable prosthesis includes a generally tubular substrate having inner and outer surfaces, and a continuous shape memory member disposed over the outer surface of the substrate along a longitudinal axis from a first end to a second end so that the member is exposed to ambient environment, the shape memory member including a series of zig-zag struts alternating between a first strut with a first length and a second strut with a second length different from the first length, adjacent first and second struts connected at one end thereof to form a first angle therebetween, bisection of the angle by a line parallel to the longitudinal axis forming a second angle between the line and the first strut and a third angle substantially equivalent to the second angle between the line and the second strut.

In another embodiment, a stent-graft includes a longitudinally compressed, generally tubular substrate having a first end and a second end along a longitudinal axis, a continuous member positioned over an outer surface of the substrate from the first end to the second end, the shape memory member including a series of zig-zag struts alternating between a first strut with a first length and a second strut with a second length different from the first length, adjacent first and second struts connected at one end thereof to form a first angle therebetween, bisection of the first angle by a line parallel to a longitudinal axis of the substrate forming a second angle between the line and the first strut and a third angle substantially equivalent to the second angle between the line and the second strut, and a graft member attached to at least one of the substrate and continuous member, the graft member including ultra high molecular weight polyethylene fibers woven or knitted into a generally tubular shape.

In one embodiment, a method of making a stent-graft includes positioning a generally tubular substrate having a first end and a second end over a mandrel, and locating a continuous shape memory member over an outer surface of the substrate from the first end to the second end so that the member is exposed to ambient environment, the shape memory member including a series of zig-zag struts alternating between a first strut with a first length and a second strut with a second length different from the first length, adjacent first and second struts connected at one end thereof to form a first angle therebetween, bisection of the first angle by a line parallel to a longitudinal axis of the substrate forming a second angle between the line and the first strut and a third angle substantially equivalent to the second angle between the line and the second strut.

These and other embodiments, features and advantages will become more apparent to those skilled in the art when taken with reference to the following more detailed description of the invention in conjunction with the accompanying drawings that are first briefly described.

DESCRIPTION OF THE PREFERRED EMBODIMENTS

Figure 1A:
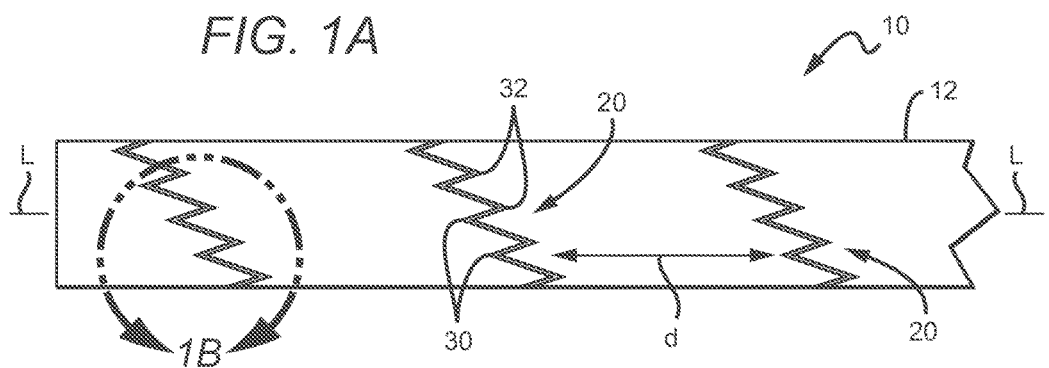
FIG. 1A is a partial perspective view of one embodiment of a stent-graft.

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

The stent-graft described herein may be utilized with bio-active agents. Bio-active agents can be coated onto a portion or the entirety of the stent and/or graft for controlled release of the agents once the stent-graft is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the stent described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

The stent may be formed of a shape memory material, including, for example, shape memory metals, shape memory alloys, super elastic shape memory metal alloys, linear elastic shape memory alloy, shape memory polymers, and combinations thereof. One preferred shape memory material is Nitinol. The stent may also be formed of metals, such as, for example, stainless steel, platinum, and Elgiloy, or certain polymers.

Potential materials for a substrate or graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a substrate material is ePTFE, while a preferred embodiment for a graft member material is high strength polymer fibers such as ultra high molecular weight polyethylene fibers (e.g., Spectra®, Dyneema Purity®, etc.) or aramid fibers (e.g., Technora®, etc.). The substrate and/or graft member may include a bioactive agent. In one embodiment, an ePTFE substrate includes a carbon component along a blood contacting surface thereof.

The examples discussed herein may include an ePTFE substrate. As is known in the art, an ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. While the preferred method used for forming an ePTFE substrate in the present invention is to extrude a tube, it should be appreciated that other forming methods are possible and are within the scope of the invention. The substrate and/or graft member of the stent-graft described herein has a thickness in the range of approximately 10 microns and approximately 100 microns, preferably in the range of approximately 20 microns and approximately 60 microns. The node-fibril microstructure of an ePTFE substrate may include various orientations for the fibrils, but in a preferred embodiment, the fibrils are oriented generally parallel to the longitudinal axis of the substrate. The average internodal distance (IND) for one preferred embodiment of a substrate and/or graft described herein is between approximately 6 microns and approximately 80 microns. Also, as described in U.S. Pat. No. 5,790,880 to Banas et al., which is incorporated by reference in its entirety in this application, the substrate and/or graft member may be made of an ePTFE that undergoes nodal elongation during radial expansion.

Referring now to FIG. 1A, a stent-graft 10 is illustrated, including a substrate 12 and a stent 20. The substrate 12 in a preferred embodiment is an extruded ePTFE tube. The stent 20 in a preferred embodiment is made of Nitinol, and more specifically, is laser cut from a Nitinol tube into an elongate member with a zig-zag strut configuration. In certain embodiments, the stent 20 includes two or more elongate members, but in a preferred embodiment, the stent includes a single elongate member. In other embodiments, the stent 20 includes discrete stent members, such as, for example, stent rings. In FIG. 1A, the elongate stent member 20 is helically wound about an outer surface of the substrate 12 such that adjacent helical windings are spaced a distance d from one another. In one embodiment, the distance d between adjacent helical windings of stent 20 is approximately equal along the length of the stent-graft 10. In other embodiments, the distance between adjacent helical windings may be varied along the length of the stent-graft 10. For example, beginning at one end of the stent-graft 10, the distance between the first two helical windings, d1, could be less than the distance d2 between subsequent helical windings. The distance between adjacent helical windings could then progressively become greater along the length of the stent-graft, could alternate between d1 and d2, etc. In embodiments including two or more elongate stent members, the members could be helically wound about the substrate in different directions and/or with different helical angles. In certain embodiments, the stent member 20 is placed under tension as it is helically wound about the substrate.

Figure 1B:
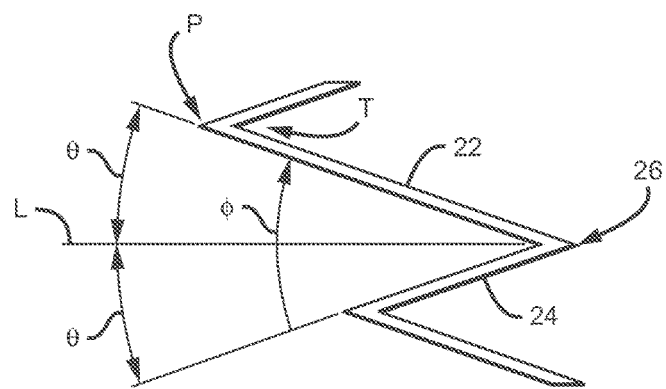
FIG. 1B is an enlarged view of one stent strut configuration of the stent-graft in FIG. 1A.

Regardless of the distance between adjacent helical windings or the direction thereof, the zig-zag struts of stent 20, in a preferred embodiment, are arranged with respect to each other and the longitudinal axis L of the stent-graft 10 as shown in FIG. 1B. Such an arrangement is believed to impart to the stent-graft 10 an ability to deploy without substantially shortening. Stent member 20 includes a plurality of zig-zag struts, including a longer first strut 22 and a shorter second strut 24 that alternate along the length of the stent member 20. The first strut 22 and second strut 24 intersect at an apex 26 to form a first angle $\Phi$ between the first and second struts 22, 24. The bisection of first angle $\Phi$ by a line parallel to the longitudinal axis L of the stent-graft 10 results in two substantially equivalent second and third angles $\theta$ as shown in FIG. 1B. Each apex 26 forms a peak P and a trough T and the stent member 20 includes a first set of apices 30 spaced from a second set of apices 32 along its length.

In one embodiment, helical windings of stent member 20 are positioned along a surface of a substrate 12 so that the peak P of apices 30 on one helical winding is aligned with a trough T of apices 30 on an adjacent helical winding, the adjacent windings spaced a sufficient distance apart to prevent interference between the windings upon radial compression of the stent-graft. For example, the stent member 20 may be attached to a substrate in an expanded configuration defining an expanded perimeter of the stent-graft 10 and subsequently radially compressed for delivery to a blood vessel to a collapsed configuration, defining a collapsed perimeter of the stent-graft 10 smaller than the expanded perimeter thereof. In another embodiment, the distance between adjacent helical windings is such that regardless of alignment, radial compression of the stent-graft will not result in interlocking of the struts.

Figure 2:
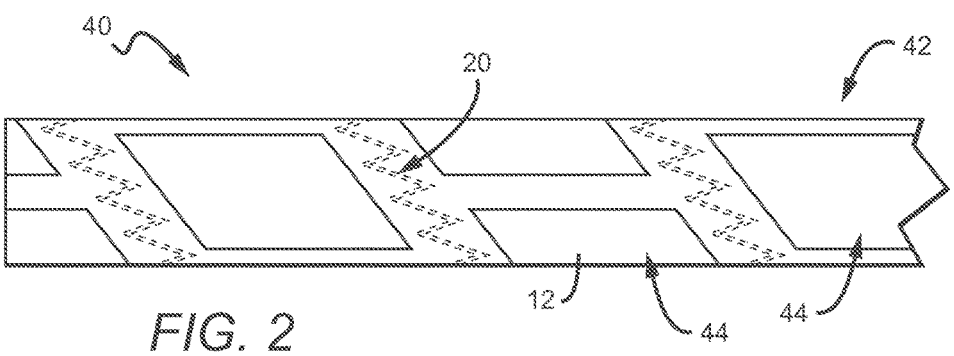
FIG. 2 is a partial perspective view of one embodiment of a stent-graft with an outer graft member.

In certain embodiments, the stent-graft will include a graft member that is disposed over the stent member 20. FIG. 2 illustrates a stent-graft 40, including an ePTFE substrate 12, an elongate stent member 20 helically wound about an outer surface of the substrate 12 such that adjacent helical windings are spaced apart along a longitudinal axis L of the stent-graft 40 and a graft member 42 positioned about the substrate 12 and stent member 20. The graft member 42 includes openings 44 that are circumferentially arranged in sets spaced apart from adjacent sets, with adjacent sets of openings offset in alternating fashion along the length of the graft member 42, as shown. It is noted that in the embodiment shown in FIG. 2, the openings 44 are configured and spaced apart such that the stent member 20 is substantially covered by the material portion of the graft member 42 (e.g., the openings include angled sides that correspond to the helical angle of the stent member with respect to the longitudinal axis of the stent-graft and these angled sides are positioned adjacent the helical windings).

The graft member in one embodiment is a continuous ePTFE member with a "lacey" graft configuration, and in another embodiment is a continuous ePTFE member with a plurality of slits, such as or similar to that described in U.S. Pat. No. 6,398,803 and U.S. Pat. No. 6,770,087 to Layne et al. In an embodiment with slits in the graft member, the slits may be relatively small such that several slits are arranged along the graft member. The slits may be arranged generally perpendicular to the longitudinal axis thereof (e.g., longitudinally adjacent slits aligned, circumferentially offset, a combination thereof, etc.), generally parallel to the longitudinal axis thereof (e.g., circumferentially adjacent slits aligned, longitudinally offset, a combination thereof, etc.), or some combination thereof. Alternatively, the slits may extend over a majority of the distance longitudinally or circumferentially of the graft member, depending on arrangement. In one embodiment the graft member 42 is arranged such that the ePTFE material is substantially covering the stent member 20, while in other embodiments the graft member 42 is arranged to reveal a small or large portion of the stent member 20.

Figure 3:
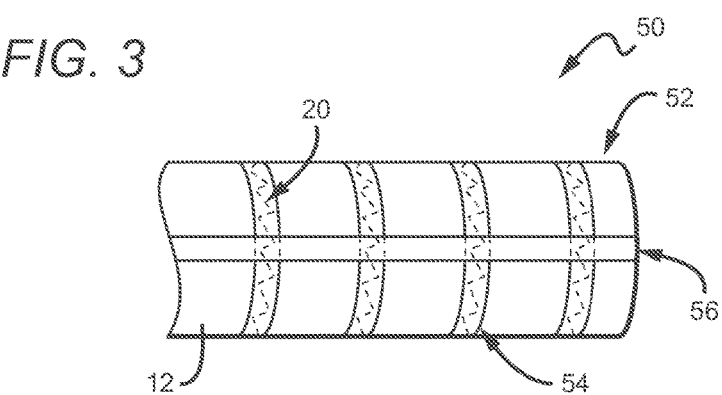
FIG. 3 is a partial perspective view of another embodiment of a stent-graft with an outer graft member.

FIG. 3 illustrates another embodiment of a graft member positioned over an ePTFE substrate 12 having an elongate stent member 20 helically wound about its outer surface. Stent-graft 50 includes a graft-member 52 having an elongate strip of ePTFE 54 that is helically wound about the substrate 12 along a substantially similar path as the stent member 20 to completely or partially cover the stent member 20, and one or more longitudinal strips of ePTFE 56 disposed transverse to the helical windings of the stent member 20 and elongate strip of ePTFE 54. The longitudinal strips 56 may be disposed over the stent member 20 prior to the winding of the elongate strip 54, subsequent to the winding of the elongate strip 54, or during the winding of the elongate strip 54 in any woven-type pattern (e.g., the longitudinal strip 56 may be alternately disposed under the elongate strip 54 and over the elongate strip 54 for adjacent windings thereof). The longitudinal strips, in one embodiment, are disposed generally parallel to the longitudinal axis of the stent-graft, but in other embodiments are positioned at an angle with respect thereto. The elongate strip 54 and/or longitudinal strips 56 may be placed under tension during disposition about the substrate 12. In one embodiment, stent-graft 50 will include an elongate strip of ePTFE 54 helically wound about the substrate 12 without any longitudinal strips 56. In another embodiment, a plurality of circumferential strips are utilized along with or in place of the helically wound elongate strip 52. Other embodiments of stent-grafts with strips and bands of ePTFE are described in U.S. Pat. No. 6,558,414 to Layne, which is incorporated by reference in its entirety in this application.

The ePTFE graft members 42, 52 in FIGS. 2 and 3, respectively, can be attached to the underlying ePTFE substrate 12 through the application of heat and/or pressure, and/or other methods, as described, for example, in U.S. Pat. No. 6,124,523 to Banas et al., which is incorporated by reference in its entirety in this application. Adhesives and/or solvents may also be used instead of, or in conjunction with, the aforementioned attachment methods. For example, a coating, such as urethane resin, could be disposed on sides of the stent member 20 to contact both the substrate and the graft member when assembled together. Thereafter, the assembly can be soaked in a solvent for bonding. Also, the stent member 20 could be sutured to the substrate at various locations along the length thereof. In one embodiment, the substrate 12 is initially unsintered ePTFE and is located over a mandrel for positioning of the stent member 20 and graft member, which may be sintered or partially sintered. The assembly is then heated to sinter the substrate to the graft member (e.g., 360 degrees C. for 10 minutes). Prior to heating, the assembly may be subject to pressures to force the separate layers together (e.g., by wrapping with a tape).

In certain embodiments, the stent-graft may include a plurality of markers arranged along its length for visualization of the stent-graft in vivo. In one embodiment, the markers include a radiopaque material, such as barium sulfate or hydroxyapatite, to increase visibility under radio imaging (e.g., x-ray).

Figure 4A:
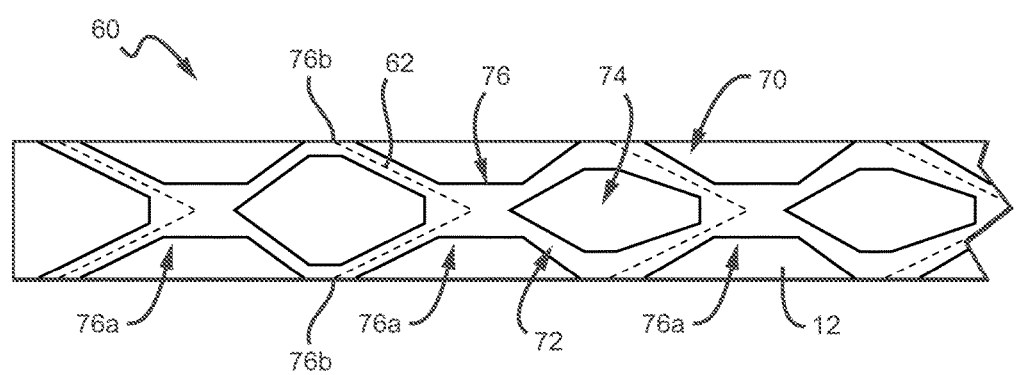
FIG. 4A is a partial perspective view of one embodiment of a stent-graft with a tensioned outer graft member.
Figure 4B:
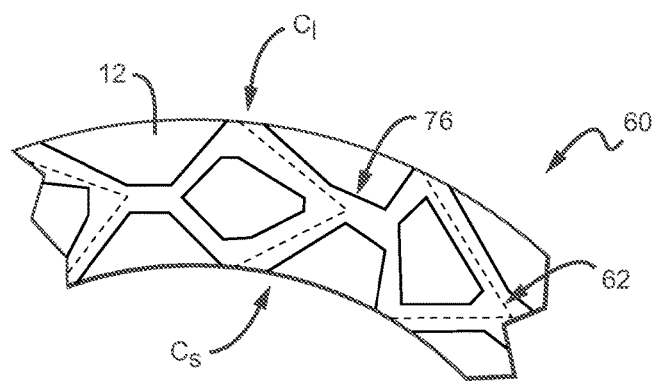
FIG. 4B is a partial perspective view of the stent-graft of FIG. 4A in a bent configuration.

FIGS. 4A and 4B illustrate a stent-graft 60 including a substrate 12, a stent member 62 and a graft member 70. The graft member 70 has a generally tubular shape and is configured in a honeycomb-type pattern or lattice structure, including a plurality of cells 72 with each cell 72 having a central opening 74. While the central opening 74 has a heptagon shape in the embodiment shown, other geometric shapes, including polygonal shapes, are possible and within the scope of the invention. The cells 72 are connected together via hinges 76, each hinge including a point of pivot to permit rotational pivoting motion thereof. In one embodiment, the hinges 76 are arranged in spaced apart sets of two, the first hinge in a given set positioned circumferentially approximately 180 degrees apart from the second hinge, and adjacent sets of hinges are rotated approximately 90 degrees from one another. Thus, for example, referring to FIG. 4A, longitudinal hinges 76a connect adjacent cells 72 in a first row of cells and adjacent cells 72 in a second row of cells located opposite the first row of cells (spaced circumferentially approximately 180 degrees therefrom), while circumferential hinges 76b, rotated approximately 90 degrees with respect to longitudinal hinges 76a, connect each cell in the first row of cells with its circumferential counterpart in the second row of cells in two locations spaced approximately 180 degrees apart (i.e., first row cells are connected to second row cells at approximately the same axial position along the longitudinal axis by two circumferential hinges).

In one embodiment, the materials for the stent-graft 60 include ePTFE for the substrate 12, shape memory material for stent 62 and a knitted or woven network of high strength polymer fibers such as ultra high molecular weight polyethylene fibers (e.g., Spectra®, Dyneema Purity®, etc.) or aramid fibers (e.g., Technora®, etc.) for graft member 70. In one method of assembly, the substrate 12 is positioned over a mandrel and longitudinally compressed in a range of approximately 50% to approximately 95% of its original, uncompressed length. While the substrate 12 is held in its compressed state, the shape memory member 62 is located thereover. For example, if the shape memory stent 62 is an elongate member including zig-zag struts, such as stent member 20, the locating step includes helical winding the shape memory member 62 about the compressed substrate 12. Once the shape memory member 62 is in position, the graft member 70 is placed over the shape memory member 62 and compressed substrate 12. The graft member 70 is then placed under tension (e.g., proximal and distal ends of the graft member are pulled in opposite directions) and clamped or otherwise fixed in place over the shape memory member 62 and compressed substrate 12. In this tensioned state, the material of the graft member 70 may cover substantially all of, or only a portion of, an outer surface of the shape memory member 62. The stent-graft 60 in its assembled form is then preferably contacted with a polymeric adhesive, such as polyurethane, to bond the graft member 70 to the shape memory member 62 and/or the substrate 12. Optionally, the polymeric adhesive can be activated by a solvent, such as tetrahydrofuran (THF). Other modes of attachment (e.g., resin, sutures, heat, pressure, etc.) may also be used in conjunction with the solvent to assist in bonding.

In FIG. 4B, a portion of the stent-graft 60 made according to the aforementioned method is shown in a curved state. Due to the longitudinal compression of the substrate 12 and flexibility of the graft member 70, the portion of the stent-graft 60 following the longer path of curvature Cl stretches, while the portion of the stent-graft 60 following the shorter path of curvature Cs compresses, such that structural integrity of the stent-graft 60 is maintained. The longitudinal hinges 76a and circumferential hinges 76b together produce a multiple hinge effect in graft member 70, which imparts enhanced flexibility to the graft member 70. The bending freedom of the substrate 12 together with the flexibility of the graft member 70 (due at least in part to the rotational freedom of the hinges 76) is believed to impart superior kink resistance to the stent-graft 60 such that the stent-graft 60 is able to navigate tortuous bends without kinking. Moreover, the graft member 70 in this embodiment acts to prevent the stent member 62 from lengthening in vivo, thereby increasing the effective radial strength of the stent member 62. This is believed to be due to one or more of the characteristics of the graft member 70, including, but not limited to, the configuration of the graft member (network of cells and hinges), the material of the graft member (high strength polymer fibers), the formation of the graft member (woven or knitted fibers), the pre-attachment tensioning of the graft member and/or the attachment of the graft member to the substrate 12 and stent member 62 through use of a solvent.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A stent-graft, comprising:
   a longitudinally compressed, generally tubular substrate having a first end and a second end along a longitudinal axis;
   a continuous member positioned over an outer surface of the substrate from the first end to the second end, the continuous member including a series of zigzag struts alternating between a first strut with a first length and a second strut with a second length different from the first length, adjacent first and second struts connected at one end thereof to form a first angle therebetween, bisection of the first angle by a line parallel to a longitudinal axis of the substrate forming a second angle between the line and the first strut, and a third angle equivalent to the second angle between the line and the second strut; and
   a graft member attached to at least one of the substrate and continuous member in a tensioned state, the graft member including polymer fibers woven or knitted into a generally tubular shape.

2. The stent-graft according to claim 1, wherein the polymer fibers are selected from a group consisting essentially of polyester, polyurethanes, fluoropolymers, ultra high molecular weight polyethylene, polyamide, aramid fibers, and combinations thereof.

3. The stent-graft according to claim 1, wherein the substrate comprises ePTFE.

4. The stent-graft according to claim 1, further comprising an adhesive disposed between the continuous member and the graft member.

5. The stent-graft according to claim 1, wherein the continuous member comprises a material selected from the group consisting essentially of stainless steel, shape memory metals, shape memory alloys, super elastic shape memory metal alloys, metal alloys, linear elastic shape memory alloy, shape memory polymers, polymers, bio-resorbable materials, and combinations thereof.

6. The stent-graft according to claim 1, wherein the graft member includes a plurality of circumferentially arranged sets of openings, adjacent sets spaced apart along a longitudinal axis of the graft member, the graft member arranged such that a surface of the continuous member is substantially covered by the graft member.

7. The stent-graft according to claim 1, wherein the graft member comprises a network of cells connected by hinges, and wherein the cells include a central opening defining a geometric shape.

8. The stent-graft according to claim 7, wherein the cells are arranged along the longitudinal axis in a first row and a second row spaced circumferentially 180 degrees from the first row.

9. The stent-graft according to claim 8, wherein adjacent cells along the first row are connected by a first longitudinal hinge and adjacent cells in the second row are connected together via a second longitudinal hinge.

10. The stent-graft according to claim 9, wherein first row cells are connected to second row cells at the same axial position along the longitudinal axis by a first circumferential hinge and a second circumferential hinge spaced 180 degrees from the first circumferential hinge.

11. The stent-graft according to claim 10, wherein the circumferential hinges are rotated 90 degrees with respect to the longitudinal hinges.

12. A stent-graft, comprising:
    a tubular substrate having a first end and a second end along a longitudinal axis, the tubular substrate having a first relaxed length and a second compressed length less than the first relaxed length;
    a continuous member positioned over an outer surface of the substrate from the first end to the second end at the second compressed length; and
    a graft member attached to at least one of the substrate and continuous member in a tensioned state, the graft member including polymer fibers woven or knitted into a generally tubular shape.

13. The stent-graft according to claim 12, wherein:
    the substrate comprises ePTFE,
    the continuous member comprises a material selected from the group consisting essentially of stainless steel, shape memory metals, shape memory alloys, super elastic shape memory metal alloys, metal alloys, linear elastic shape memory alloy, shape memory polymers, polymers, bio-resorbable materials, and combinations thereof, and the polymer fibers are selected from a group consisting essentially of polyester, polyurethanes, fluoropolymers, ultra high molecular weight polyethylene, polyamide, aramid fibers, and combinations thereof.

14. The stent-graft according to claim 12, wherein the continuous member includes a series of zigzag struts alternating between a first strut with a first length and a second strut with a second length different from the first length, adjacent first and second struts connected at one end thereof to form a first angle therebetween, bisection of the first angle by a line parallel to a longitudinal axis of the substrate forming a second angle between the line and the first strut, and a third angle equivalent to the second angle between the line and the second strut.

15. The stent-graft according to claim 12, wherein the graft member includes a plurality of circumferentially arranged sets of openings, adjacent sets spaced apart along a longitudinal axis of the graft member, the graft member arranged such that a surface of the continuous member is substantially covered by the graft member.

16. The stent-graft according to claim 12, wherein the graft member comprises a network of cells connected by hinges, and wherein the cells include a central opening defining a geometric shape.

17. The stent-graft according to claim 16, wherein the cells are arranged along the longitudinal axis in a first row and a second row spaced circumferentially 180 degrees from the first row.

18. The stent-graft according to claim 17, wherein adjacent cells along the first row are connected by a first longitudinal hinge and adjacent cells in the second row are connected together via a second longitudinal hinge.

19. The stent-graft according to claim 18, wherein first row cells are connected to second row cells at the same axial position along the longitudinal axis by a first circumferential hinge and a second circumferential hinge spaced 180 degrees from the first circumferential hinge.

20. The stent-graft according to claim 19, wherein the circumferential hinges are rotated 90 degrees with respect to the longitudinal hinges.

* * * * *